(12) United States Patent  (10) Patent No.: US 8,007,434 B2
Olson  (45) Date of Patent: Aug. 30, 2011

(54) VARIABLE STIFFNESS MEDICAL DEVICE SHAFT

(75) Inventor: Gregory Olson, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1242 days.

(21) Appl. No.: 11/276,561

(22) Filed: Mar. 6, 2006

(65) Prior Publication Data

US 2007/0208224 A1   Sep. 6, 2007

(51) Int. Cl.
*A61B 1/00* (2006.01)

(52) U.S. Cl. ............... 600/139; 600/141; 600/144

(58) Field of Classification Search .......... 600/139, 600/140–146, 151, 148, 149; 138/120, 124, 138/138
See application file for complete search history.

(56) References Cited

U.S. PATENT DOCUMENTS

| | | | |
|---|---|---|---|
| 4,580,551 A | 4/1986 | Siegmund et al. | |
| 4,690,175 A * | 9/1987 | Ouchi et al. | 138/131 |
| 5,308,342 A * | 5/1994 | Sepetka et al. | 604/525 |
| 5,329,923 A * | 7/1994 | Lundquist | 600/373 |
| 5,358,493 A | 10/1994 | Schweich, Jr. et al. | |
| 5,381,782 A * | 1/1995 | DeLaRama et al. | 600/149 |
| 5,437,288 A | 8/1995 | Schwartz et al. | |
| 5,477,856 A * | 12/1995 | Lundquist | 600/373 |
| 5,573,520 A | 11/1996 | Schwartz et al. | |
| 5,741,429 A | 4/1998 | Donadio, III et al. | |
| 5,772,641 A | 6/1998 | Wilson | |
| 5,833,632 A | 11/1998 | Jacobsen et al. | |
| 5,928,136 A * | 7/1999 | Barry | 600/142 |
| 6,012,494 A | 1/2000 | Balazs | |
| 6,135,992 A | 10/2000 | Wang | |
| 6,197,015 B1 | 3/2001 | Wilson | |
| 6,302,841 B1 * | 10/2001 | Hatori et al. | 600/142 |
| 6,485,411 B1 * | 11/2002 | Konstorum et al. | 600/139 |
| 6,652,508 B2 | 11/2003 | Griffin et al. | |
| 6,749,560 B1 | 6/2004 | Konstorum et al. | |
| 7,708,704 B2 * | 5/2010 | Mitelberg et al. | 600/585 |
| 7,850,623 B2 * | 12/2010 | Griffin et al. | 600/585 |
| 7,914,466 B2 * | 3/2011 | Davis et al. | 600/585 |
| 2003/0216615 A1 | 11/2003 | Ouchi | |
| 2003/0225314 A1 | 12/2003 | Guerra et al. | |
| 2004/0225186 A1 | 11/2004 | Horne, Jr. et al. | |
| 2005/0273085 A1 * | 12/2005 | Hinman et al. | 606/1 |
| 2006/0111615 A1 * | 5/2006 | Danitz et al. | 600/141 |
| 2006/0111617 A1 * | 5/2006 | Wimmer | 600/146 |
| 2006/0264904 A1 * | 11/2006 | Kerby et al. | 604/523 |

* cited by examiner

*Primary Examiner* — Linda Dvorak
*Assistant Examiner* — Alireza Nia
(74) *Attorney, Agent, or Firm* — Seager, Tufte & Wickhem LLC

(57) ABSTRACT

A medical device shaft with varying flexibility along its length is provided. The shaft includes at least first and second elongate shaft portions that have differing geometries and differing flexibilities. The elongate shaft portions can be made of different materials.

15 Claims, 3 Drawing Sheets

VARIABLE STIFFNESS MEDICAL DEVICE SHAFT

FIELD OF THE INVENTION

The present invention relates to flexible medical device shafts, and, in particular, to flexible catheter shafts having regions of differing flexibility and stiffness.

BACKGROUND

Endoscopic examination involves insertion of a flexible tube into a body cavity, often to locations deep within the body, such as the stomach, small intestine, and large intestine. In order to perform such procedures, a flexible tube is needed that fully transmits a pushing force from the proximal end to the distal end. Endoscopic examination also requires the flexible tube to translate rotational force applied to the proximal end to the distal end.

The pushability and torque response is typically provided by one or more layers surrounding a lumen. An outer coated braid is often disposed around an inner supporting tubular member that has spiral cuts cut in the wall for flexibility. In such a device, the flexibility or stiffness is often similar along the whole length of the device. After repeated flexing of such tubes, the spiral cut tube ends tend to migrate from the center out to the ends, constricting the spiral at the ends, reducing the tube's inherent flexibility, causing an undesired stiffening effect.

The degree of stiffness and flexibility desired for various portions of an endoscope shaft may depend on the body cavity into which it will be inserted, as well as the particular procedure to be performed. There exists a need for a medical device shaft having varying flexibility along its length.

SUMMARY

An aspect of the invention involves a medical device shaft for connection with a handle and for insertion within a body. The medical device shaft includes at least a first elongate shaft portion connected to a second elongate shaft portion and a lumen extending therethrough. The first and second elongate shaft portions are made of different materials, have different geometries, and have different flexibilities. In some embodiments, the shaft includes a third elongate shaft portion connected to the second elongate shaft portion, with the third elongate shaft portion being made of a different material, having a different geometry, and having a different flexibility compared to the second elongate shaft portion. The first, second, and third elongate shaft portions can be made of different materials, have different geometries, and have different flexibilities. The first and third elongate shaft portions can be made of the same material. In further embodiments, the shaft includes a fourth elongate shaft portion connected to the third elongate shaft portion. In such embodiments, the fourth elongate shaft portion can be made of a different material, have a different geometry, and have a different flexibility compared to the third elongate shaft portion.

The first and second elongate shaft portions can be connected by a mechanical connection, such as a friction fit, a male-female connection, or threading. In other embodiments, the first and second elongate shaft portions are connected by laser welding or an adhesive. The first and second elongate portions may each include a locking member on at least one end, with the locking member on the first elongate shaft portion being configured to couple with the locking member on the second elongate shaft portion. The locking members can be integrally formed with the elongate portions, or the locking members can be separately manufactured and attached to the elongate portions.

The first and second elongate shaft portions can be made of thermoplastic materials, and the pattern of openings in at least one of the first and second elongate shaft portions can be formed by injection molding. The pattern of openings in at least one of the first and second elongate shaft portions can also be formed by cutting. The first and second elongate shaft portions may be tubular and have a shaft wall, and the different geometries may include different patterns of openings through the wall. In some embodiments, the geometry of at least one of the first and second elongate shaft portions varies along a length of the shaft portion.

In a further embodiment, the geometry includes a plurality of slits extending perpendicular to a longitudinal axis of the shaft. At least one of the plurality of slits, the location of slits, the frequency of slits, the orientation of the slits, the size of the slits and the depth of the slits can be varied to vary the flexibility of the shaft.

The first and second elongate shaft portions can be made of a single layer. In some embodiments, the shaft includes an outer covering surrounding the first and second elongate shaft portions. In other embodiments, the shaft includes an inner layer disposed within the lumen.

Another embodiment is a medical device shaft for connection with a handle and for insertion within a body, the device including an elongated shaft having proximal, intermediate, and distal shaft portions, each with a different stiffness and a different geometry, and a lumen extending therethrough. In a further embodiment, an endoscope shaft is provided that includes a plurality of segments joined end to end, defining a lumen therethrough, wherein each of the plurality of segments has a different flexibility. Each of the plurality of segments can be made from a different material, and each of the plurality of segments can have a different geometry.

In a further embodiment, a method of making a shaft for an endoscope is provided. The shaft includes at least a first elongate shaft portion connected to a second elongate shaft portion with a lumen extending therethrough. The method involves molding a first elongate shaft portion from a first material, the first portion having a first geometry and a first flexibility, molding a second elongate shaft portion from a second material, the second portion having a second geometry and a second flexibility, and connecting the first and second elongate shaft portions such that a lumen extends therethrough. The first and second materials are different, the first and second geometries are different, and the first and second flexibilities are different.

The step of connecting may involve laser welding the first elongate shaft portion to the second elongate shaft portion, or connecting the first and second elongate shaft portions with adhesive. In some embodiments, the steps of molding the first and second elongate shaft portions include selecting first and second materials that result in the first and second elongate shaft portions having different flexibilities. The steps of molding the first and second elongate shaft portions may also include a step of selecting first and second geometries that result in the first and second elongate shaft portions having different flexibilities. In a further embodiment, the combination of the materials selected and geometries selected results in the first and second elongate shaft portions having different flexibilities. In some embodiments, the step of selecting first and second materials includes selecting materials designed to be disposable.

Other features and advantages of the invention will be evident from reading the following detailed description, which is intended to illustrate, but not limit, the invention.

BRIEF DESCRIPTION OF THE DRAWINGS

The drawings illustrate the design and utility of preferred embodiments of the present invention, in which similar elements are referred to by common reference numerals.

DETAILED DESCRIPTION

Figure 1:
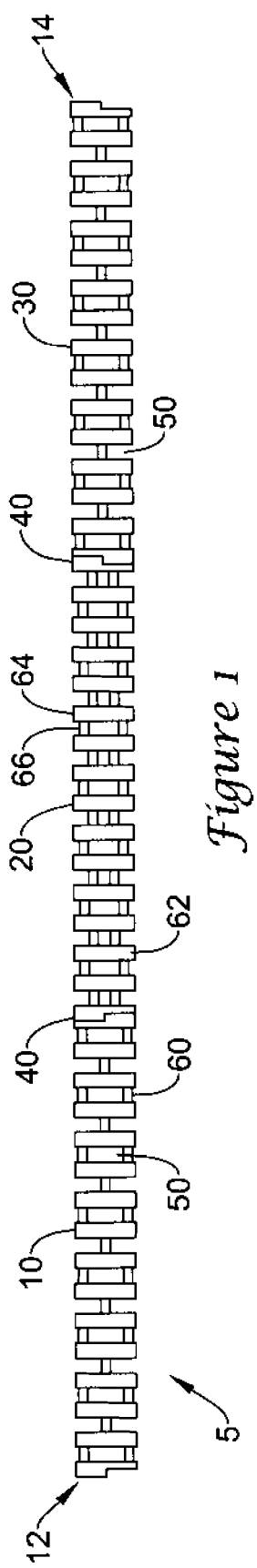
FIG. 1 is a side view of a shaft in accordance with an embodiment of the invention.
Figure 2:
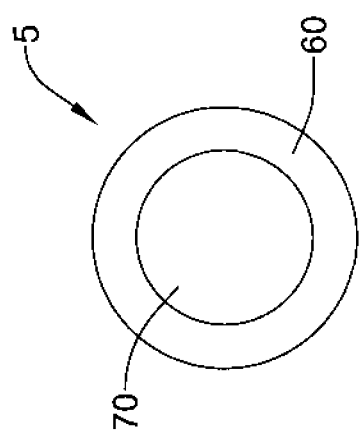
FIG. 2 is an end cross-sectional view of the shaft of FIG. 1.

With reference to FIG. 1, a shaft 5 including first 10, second 20, and third 30 elongate shaft portions is illustrated. The shaft 5 defines a lumen 70 extending from the proximal end 12 to the distal end 14. In another embodiment, the shaft 5 is made up of two elongate portions. In still further embodiments, the shaft 5 is made up of four or more elongate portions. The number of elongate portions, the materials from which the portions are made, the shaft wall thickness, and the geometry of the shaft portions are factors that contribute to the flexibility profile of the shaft 5. One or more factor is adjusted to achieve a desired flexibility profile for the shaft 5. The shaft 5 is sized and configured to be used within a body cavity of a patient. The size and flexibility profile of the shaft 5 is selected based on the particular body cavity or lumen into which the shaft 5 will be inserted.

Each elongate shaft portion 10, 20, 30 has a geometry of openings 50 through the shaft wall 60. The term "geometry" is used herein to indicate a combination of the shaft wall 60 thickness and the pattern of openings 50 and shaft wall sections 62 in the shaft 5. The geometry of the elongate shaft portions 10, 20, 30 contributes to the flexibility of the shaft 5.

In the embodiment illustrated in FIG. 1, the geometry of the elongate shaft portions 10, 20, 30 is created by a pattern of shaft wall sections 62 forming vertical bars 64 and horizontal bars 66 defining openings 50 through the shaft wall 60. In the embodiment illustrated in FIG. 1, the geometries of the first 10, second 20, and third 30 elongate shaft portions are different. The spacing and pattern of bars 64, 66 and openings 50 is different in each of the first 10, second 20, and third 30 elongate shaft portions. The three shaft portions 10, 20, 30 therefore have differing flexibilities, even if the shaft wall 60 thickness is the same and the material from which the portions are made is the same.

Figure 4:
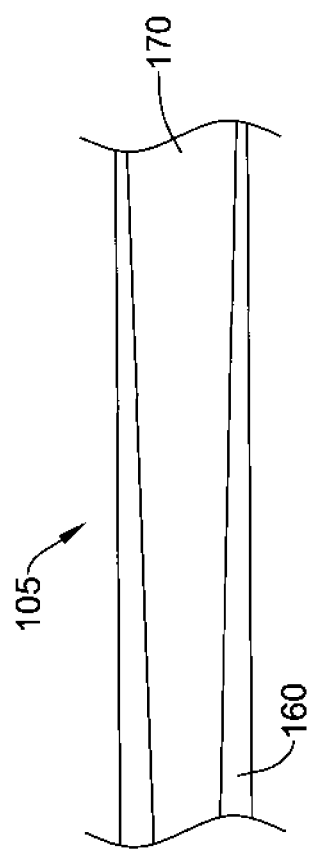
FIG. 4 is a side cross-sectional view of a shaft in accordance with another embodiment.

FIG. 4 illustrates an embodiment in which the shaft 105 has a shaft wall 160 with varying thickness. The flexibility of the shaft 105 is greater in the region where the shaft wall 160 is thinner. The outer circumference of the shaft 105 can remain constant along the length of the shaft 105. In such embodiments, the diameter of the shaft lumen 170 will vary with the varying shaft wall 160 thickness. In other embodiments, the diameter of the shaft lumen 170 remains constant and the outer circumference of the shaft 105 varies with the varying wall thickness.

Figure 5:
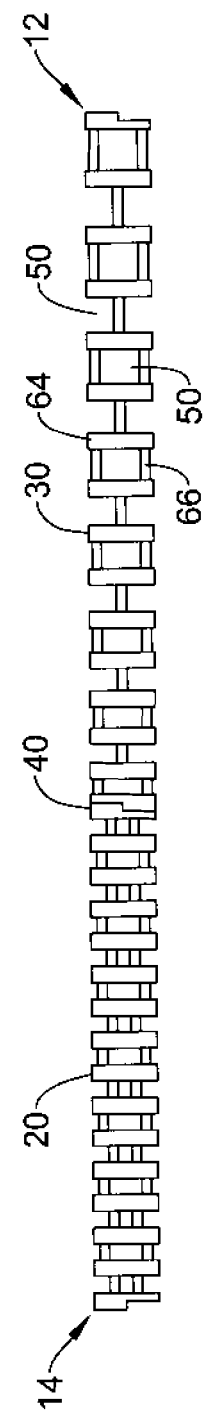
FIG. 5 is a side view of a shaft in accordance with another embodiment.

Additionally, in some embodiments, the geometry of a single elongate shaft portion varies over its length. This can be achieved by varying the shaft wall thickness along the length of the shaft portion, as illustrated in FIG. 4, or varying the pattern of shaft wall sections 62 and openings 50 in a shaft portion, as illustrated in FIG. 5. The flexibility near the proximal end 12 of shaft 5 can be less than in the second elongate shaft portion 20, and the flexibility of the third elongate shaft portion 30 can be greater than portions 10 and 20. The material, shaft wall 60 thickness, and pattern of openings 50 in the shaft wall for each shaft portion is selected to provide a desired flexibility profile along the length of the shaft 5. For example, each shaft portion 10, 20, 30 may have a unique geometry and be made of a unique material or combination of materials. The combined shaft portions 10, 20, 30 are connected to form a shaft 5 having a variable flexibility profile. The desired flexibility profile may depend on the body cavity into which the shaft 5 is to be inserted as well as the particular procedure to be performed.

Another factor in determining flexibility is the material from which the shaft is made. In some embodiments, the elongate shaft portions 10, 20, 30 are made of thermoplastic materials. In one embodiment, the shaft portions 10, 20, 30 are injection molded. The mold is designed to provide the desired geometry to the shaft portion. In another embodiment, the shaft portions are formed as tubular elements and the pattern of openings 50 in the shaft wall 60 is formed by cutting the shaft. The openings 50 can be slits cut into the shaft wall. The geometry of such a shaft portion can include a plurality of slits extending perpendicular to a longitudinal axis of the shaft. At least one of the plurality of slits, the location of slits, the frequency of slits, the orientation of the slits, the size of the slits and the depth of the slits can be varied to vary the flexibility of the shaft. The shaft portions can also be made of metal, such as Nitinol, Egiloy, NP35N, stainless steel, titanium, tantalum; or stiff polymer such as polycarbonate or polyamide. In some embodiments, the material or materials selected for making the shaft 5 are designed to be disposable.

The elongate shaft portions 10, 20, 30 have a connector on at least one end for joining the elongate shaft portions to each other. In the embodiment shown in FIG. 1, the connectors are locking members 40. A locking member 40 is disposed on the distal and proximal ends of each elongate shaft portion 10, 20, 30. The locking member 40 on the distal end of elongate shaft portion 10 connects with the locking member 40 on the proximal end of elongate shaft portion 20, and the locking member 40 on the distal end of elongate shaft portion 20 connects with the locking member 40 on the proximal end of elongate shaft portion 30, thus joining the three elongate shaft portions 10, 20, 30 to form shaft 5.

Figure 3:
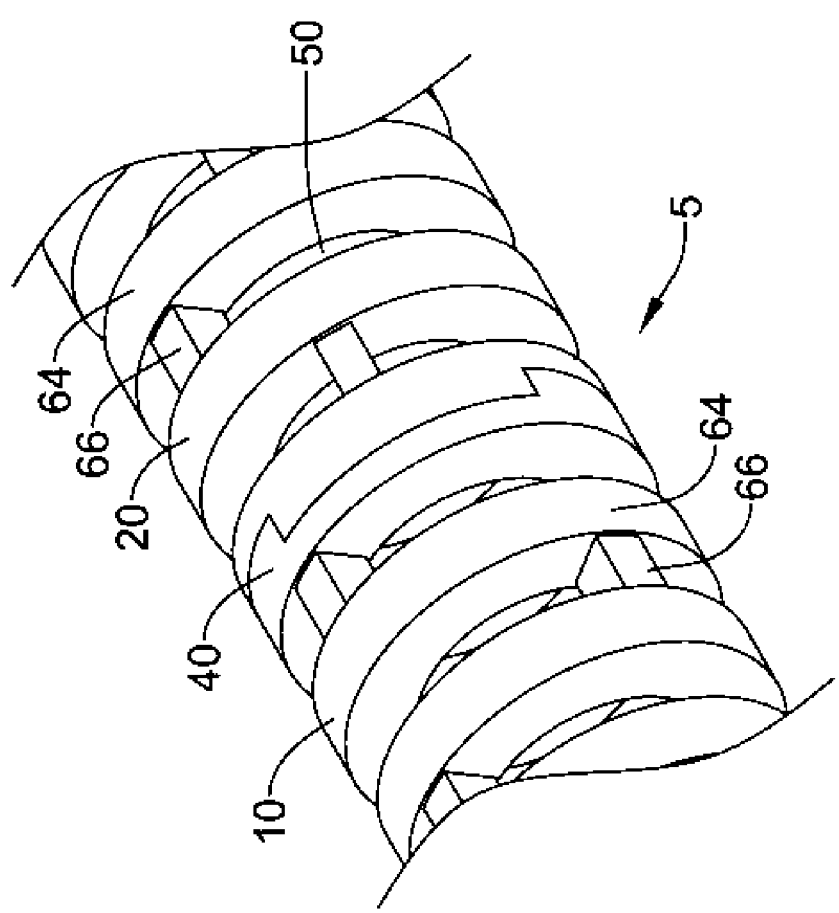
FIG. 3 is an enlarged view of a portion of the shaft illustrated in FIG. 1.

In some embodiments, the connectors are formed at the ends of the elongate shaft portions during the manufacturing process. As illustrated in FIG. 3, the locking members 40 on the elongate shaft portion 10 are a series of notches that interconnect with matching notches on elongate shaft portion 20. In other embodiments, the connectors are threaded regions at the distal and proximal ends of shaft portions 10, 20, 30. In further embodiments, the connectors are male and female connecting elements. In alternative embodiments, the connectors are attached to the elongate shaft portions when the shaft 5 is assembled, for example, with an adhesive. In still further embodiments, the connector is the end region of the elongate shaft portion that is joined to another shaft portion by friction fit, welding, such as laser welding of polymer shafts, or an adhesive.

The shaft 5 may be covered with a hydrophilic coating to aid in insertion. In some embodiments, the shaft 5 further includes at last one inner layer disposed within the lumen 70.

The shaft 5 can also include one or more outer layers. In still further embodiments, the shaft 5 can include more than one inner lumen.

A method of making a shaft for an endoscope is also provided. The shaft includes at least a first elongate shaft portion connected to a second elongate shaft portion with a lumen extending therethrough. The method involves molding the first elongate shaft portion from a first material such that the first portion has a first geometry and a first flexibility. A second elongate shaft portion is molded from a second material such that the second portion has a second geometry and a second flexibility. The first and second elongate shaft portions are then connected such that a lumen extends therethrough. The elongate shaft portions can be connected by laser welding, an adhesive, or mechanical elements such as threading, notches, or male-female connectors. The first and second materials and geometries are different, and are selected such that the first and second flexibilities are different. The materials can be selected to be disposable.

While preferred embodiments and methods have been shown and described, it will be apparent to one of ordinary skill in the art that numerous alterations may be made without departing from the spirit or scope of the invention. Therefore, the invention is not limited except in accordance with the following claims.

I claim:

1. A shaft for an endoscope comprising:
    a first elongate shaft portion, a second elongate shaft portion, and a third elongate shaft portion, each elongate shaft portion joined end to end with at least one other shaft portion such that each elongate shaft portion includes at least one end face continuously abutting at least one end face of at least one other elongate shaft portion; and
    a lumen extending therethrough;
    wherein the first and second elongate shaft portions are made of different materials, have different geometries, and have different flexibilities;
    wherein the third elongate shaft portion is made of a different material, has different geometries, and has a different flexibility compared to the second elongate shaft portion;
    wherein the first, second, and third elongate shaft portions are tubular and have a wall; and
    further comprising a fourth elongate shaft portion connected to the third elongate shaft portion, wherein the fourth elongate shaft portion is made of a different material, has different geometries, and has a different flexibility compared to the third elongate shaft portion;
    wherein the different geometries include different patterns of openings through the wall;
    wherein the geometries include a plurality of slits extending perpendicular to a longitudinal axis of the shaft, wherein at least one of the plurality of slits, the location of slits, the frequency of slits, the orientation of the slits, the size of the slits and the depth of the slits are varied to vary the flexibility of the shaft;
    wherein the first, second, and third elongate shaft portions each include a locking member on at least one end, wherein the locking member on one elongate shaft portion is configured to couple with the locking member on another elongate shaft portion.

2. The shaft of claim 1, wherein the first, second, and third elongate shaft portions are made of different materials, have different geometries, and have different flexibilities.

3. The shaft of claim 1, wherein the first and third elongate shaft portions are made of the same material.

4. The shaft of claim 1, wherein the first, second, and third elongate shaft portions are connected by a mechanical connection.

5. The shaft of claim 4, wherein the mechanical connection is selected from the group consisting of a friction fit, a male-female connection, and threading.

6. The shaft of claim 1, wherein the first, second, and third elongate shaft portions are connected by laser welding.

7. The shaft of claim 1, wherein the first, second, and third elongate shaft portions are connected by adhesive.

8. The shaft of claim 1, wherein the locking members are integrally formed with the elongate portions.

9. The shaft of claim 1, wherein the first, second, and third elongate shaft portions are made of thermoplastic materials.

10. The shaft of claim 1, wherein the geometry of at least one of the first, second, and third elongate shaft portions varies along a length of the shaft portion.

11. The shaft of claim 1, wherein the pattern of openings in at least one of the first, second, and third elongate shaft portions is formed by injection molding.

12. The shaft of claim 1, wherein the pattern of openings in at least one of the first, second, and third elongate shaft portions is formed by cutting.

13. The shaft of claim 1, wherein each of the first, second, and third elongate shaft portions is made of a single layer.

14. The shaft of claim 1, further comprising an outer covering surrounding the first, second, and third elongate shaft portions.

15. The shaft of claim 1, further comprising an inner layer disposed within the lumen.

* * * * *